US008399708B2

(12) United States Patent
Bialer et al.

(10) Patent No.: US 8,399,708 B2
(45) Date of Patent: Mar. 19, 2013

(54) COMPOUNDS USEFUL FOR TREATING BIPOLAR DISORDERS

(75) Inventors: Meir Bialer, Jerusalem (IL); Boris Yagen, Jerusalem (IL)

(73) Assignee: Yissum Research Developmemt Company of the Hebrew University of Jerusalem, Jerusalem (IL)

( * ) Notice: Subject to any disclaimer, the term of this patent is extended or adjusted under 35 U.S.C. 154(b) by 748 days.

(21) Appl. No.: 11/922,214

(22) PCT Filed: Jun. 15, 2006

(86) PCT No.: PCT/IL2006/000697
§ 371 (c)(1),
(2), (4) Date: Nov. 12, 2009

(87) PCT Pub. No.: WO2006/134600
PCT Pub. Date: Dec. 21, 2006

(65) Prior Publication Data
US 2010/0056827 A1    Mar. 4, 2010

Related U.S. Application Data

(63) Continuation of application No. 11/153,894, filed on Jun. 16, 2005, now abandoned, which is a continuation-in-part of application No. PCT/IL2004/000689, filed on Jul. 28, 2004.

(60) Provisional application No. 60/490,273, filed on Jul. 28, 2003.

(51) Int. Cl.
C07C 211/00    (2006.01)
(52) U.S. Cl. ..................................................... 564/463
(58) Field of Classification Search .................. 564/463
See application file for complete search history.

(56) References Cited

U.S. PATENT DOCUMENTS

| 3,056,726 | A | 10/1962 | Marsh |
| 5,252,339 | A | 10/1993 | Cristofori et al. |
| 5,880,157 | A | 3/1999 | Sterling et al. |
| 6,417,399 | B1 * | 7/2002 | Bialer et al. .................. 564/216 |
| 2003/0087897 | A1 | 5/2003 | Tsukamoto et al. |
| 2007/0043122 | A1 | 2/2007 | Bialer et al. |
| 2008/0081839 | A1 | 4/2008 | Bialer et al. |
| 2008/0139651 | A1 | 6/2008 | Bialer et al. |

FOREIGN PATENT DOCUMENTS

| WO | 99/54282 | 10/1999 |
| WO | 99/54282 A1 | 10/1999 |
| WO | 99/67199 A1 | 12/1999 |
| WO | 02/07677 | 1/2002 |
| WO | 03/064374 A1 | 8/2003 |
| WO | 2004/105746 A1 | 12/2004 |
| WO | 2005/009430 A1 | 2/2005 |
| WO | 2006/134600 A1 | 12/2006 |

OTHER PUBLICATIONS

Isoherranen et al. Current Opinion in Neurology, vol. 16(2), Apr. 2003, pp. 203-211.*
Blotnik et al. Drug and Metabolism and Disposition, vol. 24, No. 5, May 1996, pp. 560-564.*
Shaltiel et al (Biol. Psychiatry 56:868-878, 2004).*
Shimshoni et al (Mol. Pharmacol. 71(3): 884-892, 2007).*
Isoherranen, N., et al., "Anticonvulsant Profile and Teratogenicity of N-methyl-tetramethylcyclopropyl Carboxamide ...", Epilepsia, vol. 43, No. 2, pp. 115-126, (2002).
Radatz, M., et al., "Valnoctamide, Valpromide and Valnoctic Acid are Much Less Teratogenic in Mice than Valproic Acid", Epilepsy Research, p. 41-48, (1998).
Roeder, M., et al. "Absolute Configuration of the Four Stereoisomers of Valnoctamide (2-ethyl-3-methyl valeramide), a Potentially New Stereospecific Antiepileptic and CNS Drug", Tetrahedron Asymmetry, vol. 10, p. 841-853, (1999).
Bialer, M., et al., "Pharmokinetic Analysis and Antiepileptic Activity of Tetra-Methycyclopropane Analogues of Valpromide", Pharmaceutical Research, vol. 13, No. 2, p. 284-289, (1992).
Baillie, T., et al., "Biotransportation", Antiepileptic Drugs, p. 601-619, Raven Press, Ltd. New York, (1986).
Isherranen, N., et al., "Anticonvulsant Profile and Teratogenicity of N-methyl-tetramethylcyclopropyl Carboxamide: A New Antiepileptic Drug", Epilepsia, vol. 43, No. 2, p. 115-126, (2002).
Graul, A.J., "Compendium of Drugs for Psychiatric Disorders and Substance Abuse", Prous Science, p. 1103-1144, (2003).
Okada, A., et al., "Polycomb Homologs are Involved in Teratogenicity of Valproic Acid in Mice", Birth Defects Research, p. 870-879, (2004).
Isoherranen, N., et al., "New CNS-active Drugs Which are Second-generation Valproic Acid: Can they lead to the Development of a Magic Bullet", Seizure Disorders, p. 203-211, (2003).
Eickholt, et al., "Mood stabilizers and the cell biology of neuronal growth cones", Clinical Neuroscience Research, vol. 4, pp. 189-199, (2004).
Shimshoni, et al., "Probing CNS-Active Valproic Acid Analogues and Amide Derivatives for Mood Stabilizer Properties", unpublished manuscript, 34 pages, (2008).
Machado-Vieira, et al., "Perspectives for the development of animal models of bipolar disorder", Progress in Neuro-Psychopharmacology & Biological Psychiatry, vol. 28, pp. 209-224, (2004).
MacDonald, et al., "New Antiepileptic Drugs in Bipolar Disorder", CNS Drugs, vol. 16, No. 8, pp. 549-562, (2002).
Barel, Shimon et al., "Stereoselective Pharmacokinetic Analysis of Valnoctamide in Healthy Subjects and in Patients with Epilepsy," Clinical Pharmacology & Therapeutics, (1997), pp. 442-449, vol. 61, No. 4, Mosby-Year Book, Inc.
Bersudsky, Y. et al., "Valnoctamide as a Valproate Substitute with Low Teratogenic Potential in Mania: A Double-Blind, Controlled, Add-On Clinical Trial," Bipolar Disorders: An International Journal of Psychiatry and Neurosciences, (2010), vol. 12, pp. 376-382, The Authors & John Wiley & Sons A/S.
Bialer, Meir et al., "Valproic Acid: Second Generation," Neurotherapeutics: The Journal of the American Society for Experimental NeuroTherapeutics, (2007), pp. 130-137, vol. 4, The American Society for Experimental NeuroTherapeutics, Inc.

(Continued)

Primary Examiner — Richard Schnizer
Assistant Examiner — Audrea Buckley
(74) Attorney, Agent, or Firm — Browdy and Neimark, PLLC

(57) ABSTRACT

The invention relates to the use of valnoctamide (VCD) for the treatment of bipolar disorder and in particular for the treatment of the manic phase of the bipolar disorder.

8 Claims, No Drawings

OTHER PUBLICATIONS

Goldberg, Martin, "Effects of a New Tranquilizer, Valmethamide, in Psychiatric Outpatient Care," Diseases of the Nervous System, (1961), pp. 346-348, vol. 22.

Harl, F,-M., "Clinical Study of Valnoctamide on 70 Patients of Neuropsychiatric Consultants Under Ambulatory Treatment," La Presse Medicale, (1964), pp. 753-754, vol. 72, No. 13.

Isoherranen, Nina et al., "Pharmacokinetic-Pharmacodynamic Relationships of (2S,3S)-Valnoctamide and its Stereoisomer (2R,3S)-Valnoctamide in Rodent Models of Epilepsy," Pharmaceutical Research, (2003), pp. 1293-1301, vol. 20, No. 8, Plenum Publishing Corporation.

Kaufmann, Dan et al., "Evaluation of the Antiallodynic, Teratogenic and Pharmacokinetic Profile of Stereoisomers of Valnoctamide, an Amide Derivative of a Chiral Isomer of Valproic Acid," Neuropharmacology, (2010), pp. 1228-1236, vol. 58, Elsevier Ltd.

Mans, J. et al., "Contribution to the Study of Nirvanil (Valnoctamide) in Psychiatric Patients," Journal De Medecine De Bordeaux, (1966), pp. 394-398, vol. 143, No. 3.

Meador, Kimford, J. et al., "Antiepileptic Drug Use in Women of Childbearing Age," Epilepsy & Behavior, (2009), pp. 339-343, vol. 15, Elsevier Inc.

Melissant, CF et al., "Coma Due to an Overdose of Valnoctamide," Ned Tijdschr Geneeskd, (1992), pp. 793-794, vol. 136, No. 16, PubMed.

Merkulov, L. G., "To the Characteristics of Amide-1 Ethyl-2-Methyl-Valerianic Acid as a Drug," Archives of Biological Sciences, (1936), pp. 77-88, vol. 42, No. 3.

Nau, Heinz et al., "Valproic Acid-Induced Neural Tube Defects in Mouse and Human: Aspects of Chirality, Alternative Drug Development, Pharmacokinetics and Possible Mechanisms," Pharmacology & Toxicology, (1991), pp. 310-321, vol. 69.

Nau, H., "Valproic Acid Teratogenesis," ISI Atlas Sci: Pharmacol., (1987), pp. 52-56, vol. 1, No. 1, ProQuest.

Nau, Heinz et al., "Pharmacologic Evaluation of Various Metabolites and Analogs of Valproic Acid: Teratogenic Potencies in Mice," Fundamental and Applied Toxicology, (1986), pp. 669-676, vol. 6, The Society of Toxicology.

Nguyen, Ha T. T. et al., "Teratogenesis Associated With Antibipolar Agents," Adv Ther, (2009), pp. 281-294, vol. 26, No. 3, Springer Healthcare Communications.

Okada, Akinobu et al., "Polycomb Homologs are Involved in Teratogenicity of Valproic Acid in Mice," Birth Defects Research (Part A): Clinical and Molecular Teratology, (2004), pp. 870-879, vol. 70, Wiley-Liss, Inc.

Okada, Akinobu et al., "Amidic Modification of Valproic Acid Reduces Skeletal Teratogenicity in Mice," Birth Defects Research (Part B), (2004), pp. 47-53, vol. 71, Wiley-Liss, Inc.

Radatz, Matthias et al., "Valnoctamide, Valpromide and Valnoctic Acid Are Much Less Teratogenic in Mice Than Valproic Acid," Epilepsy Research, (1998), pp. 41-48, vol. 30, Elsevier Science B.V.

Rogawski, Michael A., "Diverse Mechanisms of Antiepileptic Drugs in the Development Pipeline," Epilepsy Research, (2006), pp. 273-294, vol. 69, Elsevier B.V.

Stepansky, William, "A Clinical Study in the Use of Valmethamide, An Anxiety-Reducing Drug," Current Therapeutic Research, (1960), pp. 144-147, vol. 2, No. 5.

Viguera, Adele C. et al., "Risk of Recurrence in Women With Bipolar Disorder During Pregnancy: Prospective Study of Mood Stabilizer Discontinuation," Am J Psychiatry, (2007), pp. 1817-1824, vol. 164, No. 12.

"Mood Ameliorating Compounds," Axiquel, (1962), McNeil Laboratories, Incorporated, Philadelphia, PA.

Davidou, P., "The Field of Action of Valnoctamide in Daily Psychiatric Practice," Toulouse Medical, (1964), pp. 1127-1158, vol. 65.

Colson, J. A., "The Place of Valnoctamide in Current Medical Practice," Toulouse Medical, (1964), pp. 969-992, vol. 65, No. 7.

Dedieu-Anglade, G., "Clinical Trial of Mi 181 (α-ethyl-β-methyl valeramide) in Gerontological Psychiatry," Therapeutique, (1963), pp. 305-308, vol. 9, R. F. G.

Roszkowski, A. P., "Behavioural and Central Muscle Relaxant Properties of 2-Ethyl-3-Methylvaleramide," Int J Neuropharmacol, (1962), pp. 423-430, vol. 1, Pergamon Press, Britain.

Merkulov, L. G., "1-Ethyl-2-Methylvaleramide as a Narcotic," Chemical Abstracts, (1937), p. 8027, vol. 31.

Macritchie, K. et al., "Valproate for Acute Mood Episodes in Bipolar Disorder," The Cochrane Database of Systematic Reviews, (2003), p. 1, John Wiley and Sons, Ltd.

Okada, Akinobu et al., "Amidic Modification of Valproic Acid Reduces Skeletal Teratogenicity in Mice," Birth Defects Res B, (2004), pp. 47-53, vol. 71, No. 1, Wiley-Liss, Inc.

"Showing Drug Card for Valproic Acid (DB00313)," www.drugbank.ca/drugs/DB00313, pp. 1-13, Aug. 25, 2010.

Merkulov, L. G., "A Characteristic of the Amide-1-Ethyl-2-Methyl-Valerianic Acid As a Narcotic," (1936), p. 143.

Hansson, Per, "Introduction: Neuropathic Pain Section," European Journal of Pain, (2002), p. 45, vol. 6, European Federation of Chapters of the International Association for the Study of Pain.

Woolf, Clifford J. et al., "Neuropathic Pain: Aetiology, Symptoms, Mechanisms, and Management," The Lancet, pp. 1959-1964, vol. 353.

Backonja, Misha-Miroslav, "Anticonvulsants (Antineuropathics) for Neuropathic Pain Syndromes," The Clinical Journal of Pain, (2000), pp. S67-S72, vol. 16, Lippincott Williams & Wilkins, Inc., Philadelphia.

Baillie, Thomas A. et al., "Valproate: Biotransformation," Antiepileptic Drugs, Third Edition, (1989), pp. 601-619, Raven Press, Ltd. New York.

Roeder, Michael et al., "Absolute Configuration of the Four Stereoisomers of Valnoctamide (2-Ethyl-3-Methyl Valeramide), A Potentially New Stereospecific Antiepileptic and CNS Drug," Tetrahedron: Asymmetry, (1999), pp. 841-853, vol. 10, Elsevier Science Ltd.

Bialer, Meir et al., "Pharmacokinetic Analysis and Antiepileptic Activity of Tetra-Methylcyclopropane Analogues of Valpromide," Pharmaceutical Research, (1996), pp. 284-289, vol. 13, No. 2.

Isoherranen, Nina et al., "Anticonvulsant Profile and Teratogenicity of N-Methyl-Tetramethylcyclopropyl Carboxamide: A New Antiepileptic Drug," Epilepsia, (2002), pp. 115-126, vol. 43, No. 2, Blackwell Publishing, Inc.

Freifelder, Morris et al., "Hydrolysis of 5,5-Disubstituted Barbituric Acids," Journal of Organic Chemistry, (1961), pp. 203-205, vol. 26.

Haj-Yehia, Abdulla et al., "Structure-Pharmacokinetic Relationships in a Series of Valpromide Derivatives With Antiepileptic Activity," Pharmaceutical Research, (1989), pp. 683-689, vol. 6, No. 8, Plenum Publishing Corporation.

Haj-Yehia, Abdulla et al., "Structure-Pharmacokinetic Relationships in a Series of Short Fatty Acid Amides That Possess Anticonvulsant Activity," The Journal of Pharmaceutical Sciences, (1990), pp. 719-724, vol. 79, No. 8, American Pharmaceutical Association.

Spiegelstein, Ofer et al., "Enantioselective Synthesis and Teratogenicity of Propylisopropyl Acetamide, A CNS-Active Chiral Amide Analogue of Valproic Acid," Chirality, (1999), pp. 645-650, vol. 11, Wiley-Liss, Inc.

Sheen, Kwangsup et al., "Signs of Neuropathic Pain Depend on Signals From Injured Nerve Fibers in a Rat Model," Brain Research, (1993), pp. 62-68, vol. 610, Elsevier Science Publishers B.V.

Kim, Sun Ho et al., "An Experimental Model for Peripheral Neuropathy Produced by Segmental Spinal Nerve Ligation in the Rat," Pain, (1992), pp. 355-363, vol. 50, Elsevier Science Publishers B.V.

Finney, D. J., "Probit Analysis," Third Edition, (1971), pp. 5-15, Cambridge University Press.

Yamaoka, Kiyoshi et al., "Statistical Moments in Pharmacokinetics," Journal of Pharmacokinetics and Biopharmaceuticals, (1978), pp. 547-558, vol. 6, No. 6, Plenum Publishing Corporation.

Gibaldi, M. et al., "Apparent Volume of Distribution," Pharmacokinetics, (1982), pp. 199-219, Marcel Dekker, New York.

Rowland, M. et al., "Pharmacologic Response," In: Clinical Pharmacokinetics, (1995), pp. 340-366.

Yanez, A., "Interaction of Midazolam and Morphine in the Spinal Cord of the Rat," Neuropharmacology, (1990), pp. 359-364, vol. 29, No. 4, Pergamon Press.

Jourdan, D. et al., "A New Automated Method of Pain Scoring in the Formalin Test in Rats," Pain, (1997), 265-270, vol. 71, Elsevier Science B.V.

McQuay, Henry et al., "Anticonvulsant Drugs for Management of Pain: A Systematic Review," British Medical Journal, (1995), pp. 1047-1052, vol. 311, British Medical Association.

Zakrzewska, Joanna M. et al., "Lamotrigine (Lamictal) in Refractory Trigeminal Neuralgia: Results From a Double-Blind Placebo Controlled Crossover Trial," Pain, (1997), pp. 223-230, vol. 73, Elsevier Science B.V.

Blom, S., Trigeminal Neuralgia: Its Treatment With a New Anticonvulsant Drug (G-32883), (1962), Preliminary Communication: The Lancet, pp. 839-840, vol. 1.

Rogawski, Michael A. et al., "The Neurobiology of Antiepileptic Drugs for the Treatment of Nonepileptic Conditions," Nature Medicine, (2004), pp. 685-692, vol. 10, No. 7.

Bialer, M. et al., "Can We Develop Improved Derivatives of Valproic Acid?" Pharmacy World & Science, (1994), pp. 2-6, vol. 16, No. 1.

White, H. S. et al., "General Principles: Discovery and Preclinical Development of Antiepileptic Drugs," Antiepileptic Drugs, 5th Edition, (2002), pp. 36-48, Lippincott Williams & Wilkins, Philadelphia.

Blotnik, Simcha et al., "Disposition of Valpromide, Valproic Acid, and Valnoctamide in the Brain, Liver, Plasma, and Urine of Rats," Drug Metabolism and Disposition, (1996), pp. 560-564, vol. 24, No. 5, The American Society for Pharmacology and Experimental Therapeutics.

Hunter, John C. et al., "The Effect of Novel Anti-Epileptic Drugs in Rat Experimental Models of Acute and Chronic Pain," European Journal of Pharmacology, (1997), pp. 153-160, vol. 324, Elsevier Science B.V.

Vajda, Frank J. E., "Gabapentin: Chemistry, Biotransformation, Pharmacokinetics, and Interactions," Antiepileptic Drugs, 5th Edition, (2002), pp. 335-339, Lippincott Williams & Wilkins, Philadelphia.

Pellock, John M. et al., "Felbamate," Antiepileptic Drugs, 5th Edition, (2002), pp. 301-318, Lippincott Williams & Wilkins, Philadelphia.

Walker, M.C. et al., "Comparison of Serum, Cerebrospinal Fluid and Brain Extracellular Fluid Pharmacokinetics of Lamotrigine," British Journal of Pharmacology, (2000), pp. 242-248, vol. 130, Macmillan Publishers Ltd.

Spina, Edoardo, "Carbamazepine: Chemistry, Biotransformation, and Pharmacokinetics," Antiepilepetic Drugs, 5th Edition, (2002), pp. 232-246, Lippincott Williams & Wilkins, Philadelphia.

Isoherranen, Nina et al., "New CNS-Active Drugs Which are Second-Generation Valproic Acid: Can They Lead to the Development of a Magic Bullet?," Current Opinion in Neurology, (2003), pp. 203-211, vol. 16, Lippincott Williams & Wilkins.

Vippagunta, Sudha R. et al., "Crystalline Solids," Advanced Drug Delivery Reviews, (2001), pp. 3-26, vol. 48, Elsevier Science B.V.

Prosecution history of U.S. Appl. No. 10/558,408, Mar. 13, 2012.

Prosecution history of U.S. Appl. No. 11/870,092, Jul. 22, 2009.

Prosecution history of U.S. Appl. No. 11/870,943, Aug. 25, 2009.

* cited by examiner

COMPOUNDS USEFUL FOR TREATING BIPOLAR DISORDERS

FIELD OF THE INVENTION

The invention relates to compounds for the treatment of bipolar disorder.

BACKGROUND OF THE INVENTION

Affective disorders are a host of psychiatric conditions that have a disturbance in mood as their predominant feature. These are for example depression, bipolar disorder (also known as manic depression), dysthymia, and cyclothymia.

A bipolar disorder is a form of a depressive disease that characteristically involves cycles of depression and elation or mania. Sometimes the mood switches from high to low and back again are dramatic and rapid switches, but more often they are gradual and slow.

Both phases of the disease are deleterious. Mania affects thinking, judgment, and social behavior in ways that may cause serious problems and embarrassment. For example, unwise business or financial decisions may be made when an individual is in a manic phase. Depression can also affect thinking, judgment, and social behavior in ways that may cause grave problems. For example, it raises the risk of suicide. Bipolar disorder is not as prevalent as some other forms of depressive disorders but it is often a chronic recurring condition.

Valproic acid (VPA) is one of the major antiepileptic drugs used today, having a wide use in both generalized and partial epilepsies. Valproic acid is a leading mood stabilizer for the treatment of bipolar disorder. Its well-known teratogenicity limits its use in young women of childbearing age.

The use of VPA is limited by its considerable adverse effects including hepatotoxicity and teratogenicity and thus cannot be given to women of childbearing age and children [Baille, T. A. et al. In Antiepileptic Drugs, eds. R. H. Levy et al. Raven Press, New York. Pp. 641-651 (1989)].

There is thus a widely recognized need for, and it would be highly advantageous to have, new agents for treating bipolar disorder devoid of the above limitations.

Valnoctamide (VCD), an amide analogue of VPA having anti-convulsant activity was found to be distinctly less teratogenic than VPA [Radatz M et al. Epilepsy Res. 1998:30(1): 41-8]. Roeder et al [M. Roeder et al, Tetrahedron: Asymmetry 1999: 10: 841-853] and U.S. Pat. No. 6,417,399 relate to stereoisomers of valnoctamide (VCD), synthesis thereof, a method for stereoselective separation thereof as well as uses thereof. The '399patent is directed to the sterioisomers and does not disclose the racemic mixture. Furthermore this application does not address specifically bipolar disorder WO 99/54282 discloses compounds for the treatment, among other of affective disorders. This application does not mention explicitly racemic VCD nor does it mention its use in the treatment of bipolar disorders.

U.S. Pat. No. 5,880,157 and Bialer et al. [M. Bialer et al. Pharm Res. 13: 284-289 (1996)] disclose derivatives of 2,2, 3,3 tetramethylcyclopropane carboxylic acid for treating epilepsy. Isoherranen et al 2002 studied the anticonvulsant activity of N-methyl-tetramethylcyclopropyl carboxamide (M-TMCD) and its metabolite in various animal (rodent) models of human epilepsy, and evaluated their ability to induce neural tube defects (NTDs) and neurotoxicity [Isoherranen N. et al. Epilepsia 2002; 43:115-126]. M-TMCD (a cyclopropyl analog of VPA) was found to be advantageous compared to VPA because of its better potency as an anticonvulsant drug, its wider safety of margin, its lack of teratogenicity and its potential lack of hepatotoxicity.

Thus, there is a widely recognized need and it will be highly advantageous to have compounds which are effective in treating bipolar disorders with minimal side effects.

OF THE INVENTION SUMMARY

The present invention is based on the use of racemic valnoctamide (VCD) for the treatment of bipolar disorder in general and the manic phase of the bipolar disorder in particular.

For purposes of this specification, the term VCD refers to 2-ethyl-3-methyl-pentanoic acid amide (Valnoctamide).

According one aspect of the present invention there is provided the use of a racemic mixture of compound of formula I

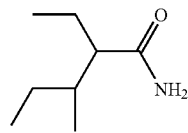

or pharmaceutically acceptable salts, hydrates and solvates thereof for the preparation of a medicament for the treatment of a bipolar disorder.

Preferably the medicament is for the treatment of the manic phase of the bipolar disorder.

According to another aspect of the present invention there is provided a pharmaceutical composition for the treatment of a bipolar disorder most preferably the manic phase of bipolar disease, comprising a pharmaceutically acceptable carrier and as an active ingredient a therapeutically effective amount of a racemic mixture of the compound of formula I or pharmaceutically acceptable salts, hydrates and solvates thereof According to yet another aspect of the present invention, there is provided a method for treating a bipolar disorder, most preferably the manic phase of bipolar disease, comprising administering to the mammal a therapeutically effective amount of a recemic mixture of compound of formula I or pharmaceutically acceptable salts, hydrates and solvates thereof.

DETAILED DESCRIPTION OF THE INVENTION

The present invention relates to the use of a compound of formula I

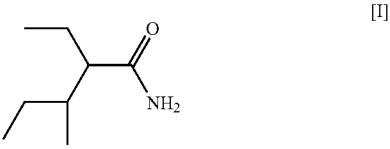

including pharmaceutically acceptable salts, hydrates and solvates thereof, for the preparation of a medicament for treating a bipolar disorder, most preferably the manic phase of bipolar disease.

The present invention additionally relates to a method for treating a bipolar disorder, most preferably the manic phase of the bipolar disorder, in a mammal comprising administering to the mammal, a therapeutically effective amount of a racemic mixture of a compound of formula I

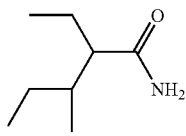

or a pharmaceutically acceptable salts, hydrates and solvates of the compound of formula I.

The present invention further concerns a pharmaceutical composition for the treatment of a bipolar disorder, preferably the manic phase of a bipolar disorder comprising a therapeutically acceptable carrier and as an active ingredient of a racemic mixture of a compound of formula I

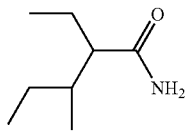

or a pharmaceutically acceptable salts, hydrates and solvates thereof.

The term "racemic mixture" refers to a mixture containing equal amounts (25%) of each of the 4 stereoisomers of the compound of formula I. As known to a person skilled in the art of organic chemistry, the compound of formula I contains two chiral carbon centers: the α and β carbons to the carbonyl groups. Each chiral or stereocenter may exist as an R or S isomer. The 4 steroisomers of the compound of formula I are therefore (2S,3S)-VCD, (2S,3R)-VCD, (2R,3R)-VCD and (2R,3R)-VCD.

Preferably the pharmaceutical composition, medicament, is adapted for oral administration and the method of administration is oral.

Preferred dosages are 600-1200mg a day, distributed by three daily administrations of 200-400 mg each.

As used herein the term "treating" includes prophylactic and/or therapeutic uses and refers to abrogating, preventing, alleviating, slowing or reversing the progression of a disease or condition, or substantially preventing the appearance of clinical symptoms of a disease or condition.

As used herein the term "psychiatric disorder" refers especially to bi-polar disorder or manic-depressive illness and especially the manic phase of a bipolar disease.

As used herein the term "therapeutically effective amount" refers to an amount of the compound sufficient to prevent, inhibit, reduce, or eliminate one or more causes, symptoms, or complications of the bipolar disease or the manic phase of the disease.

According to a preferred embodiment of the present invention the route of administration of the medicament is selected from oral, parenteral, topical, transdermal, mucosal, rectal and buccal administration.

More preferably the route of administration of the medicament is selected from oral and parenteral administration and most preferably oral administration.

More preferably the route of administration of the compound is selected from oral and parenteral administration and most preferably oral administration.

Formulations suitable for oral administration can consist of (a) liquid solutions, such as an effective amount of the compound dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodiumk talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Preferably the parenteral route of administration is selected from intravenous, intramuscular, intraperitoneal and subcutaneous administration.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. The compound can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations, include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxy-ethylenepolypropylene copolymers, (d) amphoteric detergents such as, for example, alkyl-β-aminopriopionates, and 2-alkyl-imidazoline quaternary ammonium salts, and (3) mixtures thereof.

The parenteral formulations will typically contain from about 0.5 to about 25% by weight of the active ingredient in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The compound of formula I may be made into injectable formulations. The requirements for effective pharmaceutical carriers for injectable compositions are well known to those of ordinary skill in the art. See Pharmaceutics and Pharmacy Practice, J.B. Lippincott Co., Philadelphia, Pa., Banker and Chalmers, eds., pages 238-250 (1982), and ASHP Handbook on Injectable Drugs, Toissel, 4th ed., pages 622-630 (1986).

Preferably the mammal is a human.

The invention further relates to a pharmaceutical composition for treating a bipolar disorder and especially the manic phase of a bipolar disorder comprising a pharmaceutically acceptable carrier and as an active ingredient a therapeutically effective amount of a compound of formula I as defined above.

As used herein a "pharmaceutical composition" refers to a preparation of one or more compounds described herein, with other inert chemical components such as suitable pharmaceutically acceptable carriers. The purpose of a pharmaceutical composition is to facilitate administration of a compound to a subject (mammal).

As used herein the term "pharmaceutically acceptable carrier" refers to an inert non-toxic carrier or diluent that does not cause significant irritation to a subject (mammal) and does not abrogate the biological activity and properties of the administered compound.

Examples without limitation of carriers are lactose, sucrose, water, organic solvents and polyethyleneglycol.

The carriers may include additional excipients such as binders, disintegrants, lubricants, surface active agents, preservatives and favoring agents.

The treatment may be prophylactic, for preventing the disease from occurring. Alternatively the administration may be performed after the disease or condition has already been established so as to eliminate or decrease at least one of the manifestations of the disease or condition.

Modes of Administration and Amounts

The method of administration of the compounds above may be oral, parenteral, topical, transdermal, mucosal or buccal. The pharmaceutical composition may also be administered rectally for example through the use of an enema or suppository. The term "mucosal" refers to a tissue comprising a mucous membranes, such as the nasal mucosa, pulmonary mucosa, oral mucosa (such as sublingual or buccal) or rectal mucosa. Compositions for administration through the mucosal route include for example nasal spray or nasal drops or aerosol for inhalation.

In the practice of the invention the amount of the compound incorporated in the pharmaceutical composition and the dosage may vary widely. Factors considered when determining the precise dosage are well known to those skilled in the art. Examples of such factors include, but are not limited to, age, sex and weight of the subject being treated, intended medical use of the compounds, severity of the disease, patient's general condition, the dosage form, route of administration being employed and the frequency with which the composition is to be administered.

Most preferably, the pharmaceutical composition is in the form of an oral preparation.

Because of their ease of administration, tablets and capsules are preferred and represent the most advantageous oral dosage unit form, in which case solid pharmaceutical excipients are employed. If desired, tablets may be coated by standard aqueous or non-aqueous techniques.

Preferably, the oral pharmaceutical compositions of the present invention may be administered in single or divided doses, from one to four times a day. The oral dosage forms may be conveniently presented in unit dosage forms and prepared by any methods well known manner the art of pharmacy. Preferably, the therapeutically or prophylactically effective amount of an active ingredient ranges from about 20 mg to about 2000 mg daily (preferably administered orally), more preferably from about 50 mg to about 1500 mg daily, and most preferably from 600 mg per day (200 mg three times daily) to 1200 mg (400 mg three times daily) (preferably administered orally). The daily dose may be administered either singly or in multiple dosages over 24-hour period. For oral administration, the therapeutically effective amount of the active ingredient may be several times greater than that for, parenteral administration. The amount of the orally administered active ingredient may range from about five to ten times greater than that for intravenous or subcutaneous administration.

Pharmaceutical Compositions and Dosage Forms Useful in the Invention

Pharmaceutical compositions and dosage forms which may be used in the invention comprise one or more of the active ingredients disclosed herein. Pharmaceutical compositions and dosage forms of the invention typically also comprise one or more pharmaceutically acceptable excipients or diluents (pharmaceutical acceptable carrier).

Single unit dosage forms of the invention are suitable for example for oral, mucosal (e.g., nasal, sublingual, buccal, pulmonary, or rectal mucosa), parenteral (e.g., subcutaneous, intravenous, bolus injection, intramuscular, intraarterial, intraperitoneal or subcutaneous), or transdermal administration to a patient.

Examples of dosage forms include, but are not limited to: tablets; caplets; capsules, such as soft elastic gelatin capsules; cachets; troches; lozenges; dispersions; suppositories ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions), emulsions (e.g., oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

Oral Dosage Forms Pharmaceutical Compositions

Oral dosage forms of the present invention suitable for oral administration may be presented as discrete pharmaceutical unit dosage forms, such as capsules, soft elastic gelatin capsules, tablets, caplets, cachets, or aerosols sprays, each containing a predetermined amount of the active ingredients, as a powder or granules, or as a solution or a suspension in an aqueous liquid, a non-aqueous liquid, an oil-in-water emulsion, or a water-in-oil liquid emulsion. Dosage forms such as oil-in-water emulsions typically comprise surfactants such as an anionic surfactant, for example anionic phosphate ester or lauryl sulfates, but other types of surfactants such as cationic or nonionic surfactants may be used in the compositions of the present invention. See generally, Remington's Pharmaceutical Sciences, 18th ed., Mack Publishing, Easton Pa. (1990).

Pharmaceutical compositions of the present invention suitable for oral administration may be formulated as a pharmaceutical composition in a soft elastic gelatin capsule unit dosage form by using conventional methods well known in the art. See, e.g., Ebert, Pharm. Tech, 1(5): 44-50 (1977). Pharmaceutical compositions in the form of capsules or tablets coated by an entero-soluble gastroresistant film and which contains a lyophilisate consisting of glycosaminoglyean, a thickening agent, and a surfactant have been previously described in U.S. Pat. No. 5,252,339, which is incorporated herein by reference in its entirety. Soft elastic gelatin capsules have a soft, globular gelatin shell somewhat thicker than that of hard gelatin capsules, wherein a gelatin is plasticized by the addition of plasticizing agent, e.g., glycerin, sorbitol, or a similar polyol. The hardness of the capsule shell may be changed by varying the type of gelatin used and the amounts of plasticizer and water.

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxyrnethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Preparation of the Compounds

The compounds of the present invention can be prepared according to the methods disclosed in Sterling et al (U.S. Pat. No. 5,880,157), M. Bialer et al, Pharm Res. 13: 284-289 (1996) and Freifelder et al. J. Org. Chem. 26: 203 (1961) or a modification thereof which will be apparent to those skilled in the art. The disclosures of these references are incorporated herein by reference in their Valnoctamide (VCD, powder) was given as a gift from Sanofi, France. VCD can also be obtained from ClinMeddy (Italy). VCD was synthesized as described in A. Haj Yehia and M. Bialer. Structure-pharmacokinetic relationships in a series of valpromide isomers with antiepileptic activity. Pharm. Res. 6: 683-689 (1989).

EXAMPLES

Clinical Protocols

Study design: The trial is performed in a double blind protocol

Entry criteria: patients admitted meet Diagnostic and Statistical Manual of Mental Disorders—4th edition (DSM-IV) criteria for mania or schizoaffective disorder, manic type Minimal Young Mania Scale=20, age 18-60. Both genders will participate Exclusion criteria: drug abuse, active physical illness, and of pregnancy.

Therapeutic regime : Valnoctamide(VCD) or placebo will be administered for a period of 5 week at doses of 600 mg per, day (200 mg three times daily) and increased to 1200 mg (400 mg three times daily).

Other drugs administered: no wash out of previous medications is required however patients who received depot neuroleptics within the past 2 weeks or more than 300 mg of chlorpromazine equivalents in the past three days are excluded. Patients admitted to the study are treated with risperidone beginning with 2 mg daily on days 1 and 2. On days 5 to study end the dose is increased to a maximum of 6 mg daily or decreased to a minimum of 1 mg.

Assessment: Weekly ratings by a psychiatrist blind to the study drug are conducted using the Brief Psychiatric Rating Scale (BPRS), the Young Mania Rating Scale (YMS), and the Clinical Global Impression (CGI). Weekly blood is drawn for drug levels of valnoctamide to be measured by gas chromatography While this invention has been shown and described with reference to preferred embodiments thereof, it will be understood by those skilled in the art that many alternatives, modifications and variations may be made thereto without departing from the spirit and scope of the invention. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference References BIALER, M., HAJ-YEHIA, A., BADIR, K. & HADAD, S. (1994). Can we develop improved derivatives of valproic acid. *Pharm. World Sci.* 16, 2-6.

BLOTNIK, S., BERGMAN, F., & BIALER, M., (1996). Disposition of valpromide, valproic acid and valnoctamide in the brain, liver, plasma and urine of rats. *Drug Metab. Disposit.*, 24, 560-564.

HUNTER, J. C., GOGAS, K. R., HEDLEY, L. R., JACOBSON, L. O., KASSOTAKIS, L., TOMPSON, J., & FONTANA, D. J. (1997). The effect of novel anti-epileptic drugs in rat experimental models of acute and chronic pain. *Eur. J. Pharmacol,* 324,153-160.

VAJDA, F. J. E. (2002). Gabapentin-Chemistry, biotarnsoformation, pharmacokinetics and interactions. in: *Antiepileptic drugs.* 5$^{th}$ edit. Levy, R. H., Mattson, R. H., Meldrum, B. S., & Perucca, E., eds., pp. 335-339. Philadelphia: Lippincott Williams & Wilkins.

PELLOCK, J. M., PERHACH, J. L., & SOFIA, R. D. (2002). Felbamate. in: *Antiepileptic drugs.* 5$^{th}$ edit. Levy, R. H., Mattson, R. H., Meldrum, B. S., & Perucca, E., eds. pp.301-18 Philadelphia: Lippincott Williams & Wilkins.

WALKER, M. C., TONG, X., PERRY, H., ALAVIJEH, M. S., & PATSALOS, P. N. (2000). Comparison of serum, cerebrospinal fluid and brain extracellular fluid pharmacokinetics of lamotrigine. *Br. J. Pharmacol.* 130, 242-248.

SPINA E. (2002). Carbamazepine-Chemistry, biotarnsoformation, pharmacokinetics and interactions. in: *Antiepileptic drugs.* 5$^{th}$ edit. Levy, R. H., Mattson, R. H., Meldrum, B. S., & Perucca, E., eds., pp. 232-246. Philadelphia: Lippincott Williams & Wilkins. MES, maximal electro-shock; ED$_{50}$, median effective dose; SNL, spinal nerve ligation; NE, no effect; NT, not tested; CBZ, carbamazepine; FBM, felbamate; LTG, lamotrigine.

Belmaker R H (2004) Bipolar disorder *N. Eng. J. Med* 351: 476-486.

Amann B and Grunze H (2005), Neurochemical underpinning in bipolar disorder and epilepsy. *Epilepsia* 46 Suppl 4: 26-30

Gurvich Nadia and Klein Peter, (2002) Lithium and valproic acid: parallels and contrasts in diverse signaling contexts, Pharmacology & Therapeutics 96: 45-66

What is claimed:

1. A method for treating a bipolar disorder, comprising: administering to a subject suffering from bipolar disorder an active ingredient comprising a racemic mixture of a compound of formula I

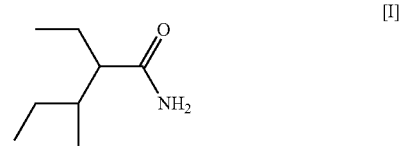

or a pharmaceutically acceptable salt, hydrate or solvate thereof.

2. The method according to claim 1, wherein said administering is during a manic phase of the bipolar disorder.

3. The method according to claim 1, wherein said administering comprises administering through a route of administration selected from the group consisting of oral, parenteral, topical, transdermal, mucosal, rectal and buccal.

4. The method according to claim 1, wherein said administering comprises oral administration.

5. The method according to claim 1, wherein said administering comprises parenteral administration.

6. The method according to claim 5, wherein said parenteral administration comprises administering by an administration route selected from the group consisting of intravenous, intramuscular, intraperitoneal and subcutaneous.

7. The method according to claim 1, wherein the active ingredient is administered in an amount of 200 mg.

8. The method according to claim 1, wherein the active ingredient is administered in an amount of 400 mg.

* * * * *